United States Patent
Stefas

(10) Patent No.: US 8,986,925 B2
(45) Date of Patent: Mar. 24, 2015

(54) METHOD FOR IN VITRO DETECTION AND/OR QUANTIFICATION AND/OR IDENTIFICATION OF INFECTIOUS COMPOUNDS IN A BIOLOGICAL MATERIAL

(75) Inventor: Ilias Stefas, La Grande Motte (FR)

(73) Assignee: Apoh Technologies SA, La Grande Motte (FR)

( * ) Notice: Subject to any disclaimer, the term of this patent is extended or adjusted under 35 U.S.C. 154(b) by 973 days.

(21) Appl. No.: 12/865,830

(22) PCT Filed: Jan. 30, 2009

(86) PCT No.: PCT/FR2009/000104
§ 371 (c)(1),
(2), (4) Date: Dec. 22, 2010

(87) PCT Pub. No.: WO2009/112701
PCT Pub. Date: Sep. 17, 2009

(65) Prior Publication Data
US 2011/0111390 A1 May 12, 2011

(30) Foreign Application Priority Data
Feb. 1, 2008 (FR) ...................... 08 00553

(51) Int. Cl.
| *C12Q 1/70* | (2006.01) |
| *C12Q 1/68* | (2006.01) |
| *G01N 33/569* | (2006.01) |
| *C12Q 1/04* | (2006.01) |

(52) U.S. Cl.
CPC ............ *G01N 33/56983* (2013.01); *C12Q 1/04* (2013.01); *G01N 33/56911* (2013.01)
USPC ................. 435/5; 435/6.1; 435/6.12

(58) Field of Classification Search
None
See application file for complete search history.

(56) References Cited

U.S. PATENT DOCUMENTS 5,650,269 A * 7/1997 Rucheton et al. ................. 435/5
6,465,191 B1 10/2002 Stefas et al.

FOREIGN PATENT DOCUMENTS

| EP | 0775315 A1 | 5/1997 |
| FR | 2723203 A1 | 2/1996 |
| FR | 2723204 A1 | 2/1996 |
| WO | W09418569 A1 | 8/1994 |

OTHER PUBLICATIONS

Iwata et al. (Biological and Pharmaceutical Bulletin. 2003; 26 (8): 1065-1069).*
Gushiken et al., Polymorphisms β2-glycoprotein I: phospholipid binding and multimeric structure, Thrombosis Research, 108:175-180 (2003).
Matsuura et al., Anticardiolipin antibodies recognize β2-glycoprotein I structure altered by interacting with an oxygen modified solid phase surface, J. Exp. Med., 179:457-462 (1994).
Uchida et al., Optimization of the virus concentration method using polyethyleneimine-conjugated magnetic beads and its application to the detection of human hepatitis A, B and C viruses, Journal of Virological Methods, 143:95-103 (2007).

* cited by examiner

*Primary Examiner* — Shanon A Foley
(74) *Attorney, Agent, or Firm* — Browdy and Neimark, PLLC

(57) ABSTRACT

Method for in vitro detection and/or quantification and/or identification of infectious compounds present in a fluid medium M constituting a biological material, in which method a suspension of microbeads of solid polymer material capable of binding proteins is prepared; the microbeads are loaded with β2GPI proteins by coupling with a sufficient amount of β2GPI proteins; said microbeads are brought into contact with the fluid medium M while adding ions of at least one oxidizing metal, so as to bind the infectious compounds to the β2GPI proteins; the microbeads thus prepared are separated from their suspension medium, so as to obtain a residue; and the infectious compounds of the residue are detected and/or quantified and/or identified.

13 Claims, 4 Drawing Sheets

Figure 1:
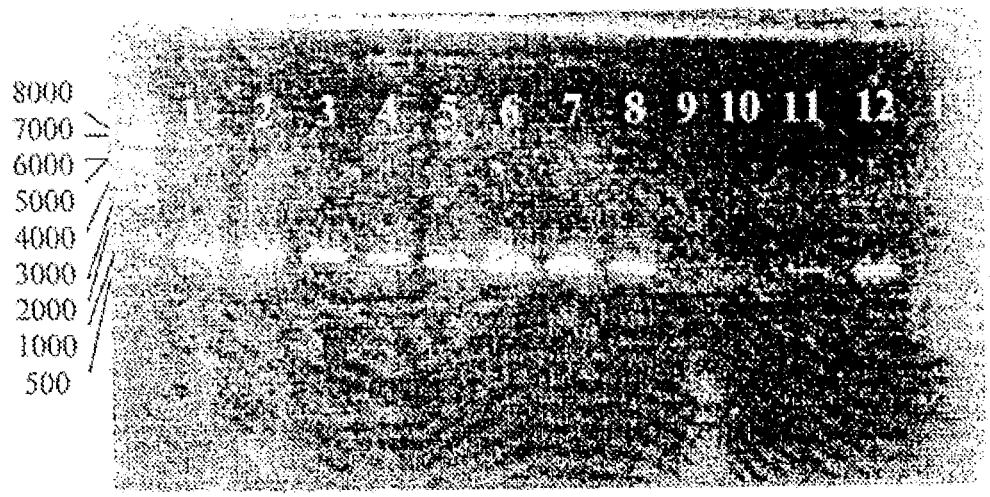

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: Synthetic

<400> SEQUENCE: 1
gtgctgcaga gagtttgatc ctggctcag                               29

<210> SEQ ID NO 2
<211> LENGTH: 31
<212> TYPE: DNA
<213> ORGANISM: Artificial Sequence
```

-continued

```
<220> FEATURE:
<223> OTHER INFORMATION: Synthetic

<400> SEQUENCE: 2
cacggatcct acgggtacct tgttacgact t                              31

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ctctttacca tgaagatacc cacc                                      24

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gtgcacggct taccattttt                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
caagcaccct atcaggcagt                                           20

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
agcgtctagc catggcgt                                             18
```

METHOD FOR IN VITRO DETECTION AND/OR QUANTIFICATION AND/OR IDENTIFICATION OF INFECTIOUS COMPOUNDS IN A BIOLOGICAL MATERIAL

The present invention relates to a method for in vitro detection and/or quantification and/or identification of infectious compounds in a biological material In the present patent application, by "biological material" is meant a biological tissue, a preparation or an extract originating from biological tissue, liquid or solid, or a medium, natural or not, capable of containing infectious compounds, for example flowing water or water for rinsing fruits and vegetables. Such a material can also be a mixture of at least two materials as defined above; it can therefore be, in particular, either prepared from tissues, organs, stools or body fluids from a patient suffering from an infection, or obtained from "in vitro" cultures; such biological material can be also a serum, plasma, urine, cerebrospinal fluid, synovial fluid, peritoneal fluid, pleural fluid, seminal fluid or acetic fluid.

In the present patent application, by infectious compounds, hereafter generically abbreviated to "ICs", is meant both compounds, in particular proteinaceous, constituting an infectious agent, and structures which contain infectious compounds. These structures are, in particular, complete or incomplete, endogenous or exogenous, infectious agents, their metabolites or also assemblies containing constitutive compounds of these infectious agents, assemblies which have certain properties of said infectious agents, in particular the property of being detected by certain antibodies specific to infectious compounds; the ICs can also be compounds specifically induced in the organism by the IC defined previously, or by the expression of genes being expressed in abnormal manner. Among the ICs there may be mentioned, for example, viruses, bacteria, fungi, mycoplasmas, parasites and abnormal animal cells.

A plasma glycoprotein called β2-glycoprotein I, or also abbreviated to "β2GPI", has already been described; the sequence of this human glycoprotein has in particular been referred to in the articles by J. LOZIER et al., Proc. Natl. Acad. Sci. ISA, Vol. 81, p. 3640-3644 (July 1984) and by T. KRISTENSEN et al., FEBS Letters, Vol. 289, p. 183-186 (1991). It has been noted that this β2GPI protein exhibits polymorphism: the name β2GPI is considered hereafter as generic for all forms.

In the international application WO 94/18569, it was pointed out that certain, in particular proteinaceous, infectious compounds bound to the form of β2GPI which had been described in French patent 2 701 263. In the document WO 94/18569, a method for detection and/or assay of viral compounds is proposed, in which the infectious viral compounds are bound to the form of β2GPI used; therefore this form of β2GPI is added to infectious viral compounds contained in a biological material, so as to separate the viral compounds thus captured in order to then detect them and/or assay them. In European patent EP 775 315, the formation of a complex between an infectious, in particular proteinaceous, compound and any form of β2GPI is described; the infectious compound could, in particular, be a bacterium. It is clear from these documents that the β2GPI is capable of binding to a flat solid support, such as the bottom of wells in a microtitration plate, and that the β2GPI thus adhering to this flat solid support, is capable of binding to the infectious compounds (ICs) present in clinical, biological or environmental samples at very low concentrations. It is known, moreover, that such samples can contain substances inhibiting, at least partially, the detection of pathogens, substances which, as a result, can reduce the sensitivity of the detection. It is therefore important to be able to capture and concentrate these pathogens in order to eliminate the substances which inhibit their detection.

The studies of the Applicant company have shown that the binding of the β2GPI to the bottom of the wells in the titration plates, took place thanks to a particular conformation of the β2GPI, a conformation which subsequently allowed the formation of a complex of the β2GPI with an infectious compound. The literature had moreover reported that the conformation of the β2GPI varied at its binding to a solid surface (Matsuura et al., J. Exp. Med. 179, p. 457-462 (1994). A method for the concentration of viruses had already been described (A. IWATA et al., Biol. Pharm. Bull. 26(8), p. 1065-1069 (2003)), using sulphonated magnetic microbeads to which the viruses would adhere, the concentration of the viruses being obtained due to the fact that the microbeads were magnetic and could be separated from the infectious medium by the action of a magnetic field. Unfortunately, the result of this technique was essentially a function of the adhesion of the viruses to the microbeads. This document explains in detail that certain non-enveloped viruses do not bind to microbeads made of polyethylene-imine and that it is necessary to use sulphonated microbeads in order to concentrate certain viruses. Moreover, for certain viruses, it was necessary to add bivalent cations, such as $Zn^{2+}$ or $Cu^{2+}$ to the medium. It follows from this finding that, depending on the nature of the virus, the polymer constituting the microbeads must be different, grafted or not grafted, and that bivalent ions are necessary or not necessary; the beads must therefore be prepared on an ad hoc basis depending on the virus to be concentrated. The same findings emerge from the document by E. UCHIDA et al., Journal of Virological Methods, 143, p. 95-103 (2007), which relates to the concentration of the human hepatitis A, B, and C viruses. In the presence of a sample containing an unidentified virus to be detected, it was therefore not possible to determine what kind of microbeads was capable of giving rise to an adhesion of the virus of interest.

Consequently, given the abovementioned drawbacks, a person skilled in the art would have been inclined to research favourable environmental conditions such that the microbeads could adhere to the infectious compounds whatever their nature or their identity. This is moreover the approach followed by UCHIDA in the abovementioned article, describing the conditions particularly favourable to the direct capture of the HAV, HBV and HCV viruses. The Applicant company has however gone against this approach by proposing, according to the present invention, to interpose a molecule of β2GPI between a microbead and an infectious compound (IC) to be bonded above it. The state of the art has made it possible to determine the nature of the solid supports allowing good adhesion of the protein β2GPI; the binding of the β2GPI to a microbead is then carried out without the polymer of the microbead having to be modified depending on the infectious compound to be bonded subsequently. And, moreover, it was noted that the binding of the β2GPI to the microbead did not disturb the adhesion of the infectious compound to the β2GPI; now, this last point was completely unexpected as it could not be foreseen that the conformation of the β2GPI bonded to a microbead, would allow the adhesion of a pathogenic agent to the glycoprotein. Incidentally and complementarily, a dissuasive element as regards arriving at the invention resulted from the fact that it was known that β2GPI had a tendency to self-polymerize (see: Thrombosis Research, 108, p. 175-180 (2003)), which risked leading to an agglutination of the microbeads carrying β2GPI, an agglutination which, of course, made the binding of pathogenic agents to the molecules of β2GPI unthinkable.

Finally, it was noted, according to the invention, that the adhesion of the infectious compounds to microbeads loaded with β2GPI made it possible, in certain cases, by direct contact of the microbeads loaded with β2GPI and ICs with an appropriate medium, to detect, quantify or identify adhering ICs. In the case of viruses, said medium is a culture of cells capable of being infected by the viruses captured by the microbeads.

According to another aspect of the invention, the Applicant company also sought, in parallel, to ensure good adhesion of the ICs to the microbeads loaded with β2GPI by acting on the environment where this adhesion occurs; it noted that this purpose was achieved when ions of an oxidizing metal were added to the adhesion medium, irrespective of the nature of the ICs, in particular viruses or bacteria. These metals include $Cu^{2+}$ but this effect is not due to the fact that the Cu is divalent (contrary to what one might think on studying the abovementioned IWATA publication) as IWATA mentions that he obtains a satisfactory result with $Zn^{2+}$ or $Cu^{2+}$ whereas the Applicant has noted that, for the implementation of the invention, Zn does not produce significant results. It had moreover already been pointed out that the presence of Zn or Fe ions was unfavourable to the adhesion of the viruses to the β2GPI (STEFAS et al., Hepatology, 33(1), pages 207-217 (2001)); now the presence of magnetic elements in the microbeads can generate an unfavourable diffusion of iron ions in the suspension medium of the microbeads. The Applicant company noted no significant effect unfavourable to the binding of the ICs to the β2GPI when the presence of oxidizing ions in the medium is ensured.

BRIEF DESCRIPTION OF THE DRAWINGS

FIG. 1 shows electrophoresis of DNAs obtained using PCR on 2% agarose gel containing ethidium bromide. Tracks 1 to 13 represent the experiments listed in Table II.

FIG. 2 shows electrophoresis and Southern blot of DNAs from RT-PCR of viral nucleic acids in serum samples of patients infected with hepatitis C virus.

FIG. 3 shows the gel electrophoresis results obtained for tracks 1 to 16 from Table III.

FIG. 4 shows the gel electrophoresis results obtained for tracks 1 to 6 from Table IV.

FIG. 5 shows H3N2 influenza virus infection of MDCK cells in petri dishes by staining cells to verify cytopathogenic effect of the virus.

FIGS. 6A and 6B show localization of MDCK cells carrying viral proteins by immunofluorescence with fluorescent monoclonal antibodies that recognize the viral proteins.

FIGS. 7A-7C show virus infection of Hep2 cells by immunofluorescence, where the virus of the vaccine has been captured by microbeads loaded with β2GP1 (FIG. 7A), the virus of the vaccine in the absence of microbeads loaded with β2GP1 (FIG. 7B), and the cells are brought into contact with the washing buffer of the microbeads after they have been loaded with β2GP1 and viruses of the vaccine (FIG. 7C).

A subject of the present invention is consequently an in vitro method for detection and/or quantification and/or identification of infectious compounds present in a fluid medium M constituting a biological material, a method in which, in a known manner, a suspension of microbeads in a liquid suspension medium is prepared, said microbeads being delimited by an outer surface constituted by a solid polymer material capable of binding proteins, characterized by the fact that it comprises the following stages:

a) a loading of the microbeads in the suspension with β2GPI proteins is ensured by coupling with a sufficient quantity of β2GPI proteins, either passively in a suspension medium or using a known chemical binding protocol;

b) in a container, said microbeads loaded with β2GPI proteins are brought into contact with the fluid medium M by adding ions of at least one oxidizing metal, under appropriate conditions in order to ensure sufficient binding of the infectious compounds to the β2GPI proteins carried by the microbeads;

c) the microbeads thus prepared are separated from their suspension medium, said suspension medium is removed from the container in order to obtain, optionally after a washing with a buffer, a residue with a high concentration of infectious compounds;

d) and the infectious compounds are detected and/or quantified and/or identified, starting from the concentrated residue thus obtained.

Preferably, the oxidizing metal ions which, in stage b) of the method according to the invention, are added to the medium M, are copper ions, the concentration of copper ions in said medium being comprised, after said addition, between 1 and 100 mM.

Advantageously, stage d) of the method according to the invention defined above is carried out by a means taken from the group formed by infectivity, a specific enzymatic reaction, a fluorescent or radiolabelled tracer, a detection of specific nucleic acids by hybridization with a labelled probe, a PCR or RT-PCR reaction, an assay, a count, a visualization, an optical method, electron or non-electron microscopy.

The infectious compounds (ICs); can, in particular, be bacteria.

In the case where the ICs are bacteria, it is possible to detect and/or quantify and/or identify them by optical density reading, by ATP-metry or by PCR ("polymerase chain reaction").

In the case where the ICs are viruses, starting from the concentrated residue obtained on completion of stage c) of the method, the nucleic acids of the ICs of interest are extracted by lysis, followed by PCR amplification (or RT-PCR if the viruses of interest are retroviruses) of the nucleic acids of the ICs of interest by using the primers appropriate to said ICs of interest and visualization on gel of the nucleic acids optionally obtained in order to define the presence or the absence of the ICs of interest and/or in order to quantify the load of said ICs of interest in the medium M. Advantageously, in order to detect and/or identify viruses of interest bound to microbeads obtained according to stage c) of the method according to the invention, the residue is resuspended, its microbeads are brought into contact with cells sensitive to the virus of interest, said cells are placed in culture and any infection of the cells by the viruses of interest is observed. In order to detect an infection of cells, it is possible, for example, to observe the cytopathological effect of the infectious compound after appropriate staining of the cells or also to observe the immunofluorescence after binding of the cells and reaction with fluorescent antibodies, which recognize proteins corresponding to the presence of the infectious compounds.

The solid material constituting the outer surface of the microbeads is preferably chosen from the group formed by the plastics and the elastomers, said material carrying or not carrying reactive groups grafted to the outer surface of the microbeads in order to ensure a chemical bond to the β2GPI proteins; the microbeads can advantageously have a substantially spherical shape and an average diameter comprised between 1 and 100,000 nm. According to a first variant, the microbeads are separated from their suspension medium by centrifugation; but according to a second preferred variant, microbeads having a core formed by one (or more) particle(s) of magnetic material in order to allow their separation from the suspension medium using a magnetic field are chosen. Such magnetic microbeads are commercially available: for example, they are constituted by a magnetic core covered with a polymer matrix made of polystyrene. The magnetic field allowing the separation of the microbeads from their suspension medium can be created by a simple permanent magnet which is moved close to the container in order to carry out stage c) of the method according to the invention.

The choice of the material constituting the microbeads is limited only by its ability to couple the β2GPI: it is possible, for example, to use magnetic microbeads sold by MERCK under the trade name "Estapor(R) superparamagnetic microspheres". As indicated previously, the coupling of the β2GPI to the microbeads can be carried out either passively, or by using a chemical coupling protocol. In order to achieve passive coupling with microbeads, in particular the abovementioned "Estapor" (R) microbeads, the microbeads are advantageously placed in suspension in a buffer containing β2GPI, at a pH comprised between 3.5 and 10.5 and, better, between 5.5 and 9.5. The buffer used is among the buffers commonly used in biology and can, in particular, be an acetate, phosphate, borate or Tris buffer. The microbead/β2GPI mixture is, preferably, incubated at a temperature comprised between 4° C. and 40° C. for a period of time comprised between 10 nm and 24 h under stirring, preferably constant, gentle, horizontal stirring. The microbeads are subsequently separated magnetically or centrifuged and the supernatant is removed. The pellet containing the microbeads is placed in suspension in a preservation buffer, which is, preferably, the same as that used subsequently for the coupling, this buffer having a pH comprised between 6 and 9. Preferably, the loading of the microbeads with β2GPI proteins is carried out by placing them in a liquid suspension medium which contains, in aqueous solution, from $10^{-6}$ to 100 mg of β2GPI per gram of dry weight of microbeads, the concentration of β2GPI in the medium being then comprised between $10^{-5}$ and 10 μg/μl, and by stirring the suspension thus constituted for 15 to 60 nm at a temperature comprised between 30° C. and 45° C.

The sample containing the IC is brought into contact with the loaded microbeads, either directly, or after its dilution in a buffer, the pH of which is comprised between 5 and 9 or, better, between 5.6 and 8. The complex which forms between the β2GPI and the IC is advantageously, subsequently incubated for a period of time comprised between 5 nm and 24 h, preferably between 30 nm and 2 h, at a temperature comprised between 4° C. and 40° C., preferably approximately 37° C. After incubation, the sample which has not reacted with the β2GPI bound to the microbeads, is removed by centrifugation or magnetizing of the microbeads. The microbeads thus isolated can be used for the detection and/or the quantification and/or the identification of the IC. The separation and/or the assay and/or the quantification of the IC bound to the support by the β2GPI can be carried out by any known means such as infectivity, a specific enzymatic reaction, a fluorescent or radiolabelled tracer, the detection of specific nucleic acid by hybridization with a labelled probe, a polymerase chain reaction, an assay, a count, a visualization, an optical method, electron or non-electron microscopy.

In order to provide a better understanding of the subject of the invention, a description will now be given of several methods of implementation, as purely illustrative and non-limitative examples.

EXAMPLE 1

Binding of a Bacterium in Copper Medium to Microbeads Loaded with β2GPI

Firstly, the bacterium used is a strain of *Escherichia coli* (*E. coli*) supplied by the Centre de conservation de produits agricoles (CPA). A pre-culture is incubated at 37° C. for 16 h in LB (Luria Bertani) medium having the following composition:

| | |
|---|---|
| Bacto tryptone | 10 g |
| Yeast extract | 5 g |
| NaCl | 10 g pH 7.5 |
| Water | qsf 1,000 g |

This pre-culture is used immediately or stored at 4.5° C.

The microbeads intended for binding the bacteria which are used in this example are magnetic microbeads sold by MERCK under the name "Estapor(R) superparamagnetic micro spheres" which have a diameter comprised between 0.300 and 0.500 μm.

These microbeads are placed in suspension in a buffer with a pH of 6.0 containing the β2GPI. The concentration of β2GPI in this coupling buffer is 100 μg/ml; the microbeads are incubated in the buffer under constant gentle stirring at a temperature of 25° C. for 3 hours. The microbeads are then centrifuged at 1,500 rpm and the supernatant is removed; the centrifugation pellet is placed in suspension in the same buffer as that used for the subsequent coupling of the β2GPI, which forms the suspension of microbeads loaded with β2GPI to be tested.

$10^5$ bacteria of the preculture are placed in suspension either in 50 mM Tris buffer (pH 7.6), or in PBS buffer (see formulation below), or in a 50 mM sodium acetate buffer (pH 5.6 with 10 mM HCl), in the presence or absence of 2 mM of $CuSO_4$, or in an LB medium; the different suspensions of *E. coli* are placed in 1 ml haemolysis tubes with a constant quantity of microbeads (10 μl). The tubes are incubated at 37° C. for 60 nm, under horizontal stirring. In each tube, the microbeads are then separated from the liquid phase by means of a permanent magnet placed externally against the wall of the tube and the supernatant is removed. The microbeads are then washed twice with sterile PBS having the following formulation:

| | |
|---|---|
| NaCl | 80 g |
| KCl | 74.562 g |
| $KH_2PO_2$ | 2.4 g |
| $Na_2HPO_4/2H_2O$ | 29 g |
| Water | qsf 1,000 g |

The presence of bacteria is assessed by PCR. Table I summarizes the results obtained:

TABLE I

| Buffer | PCR |
|---|---|
| Tris | + |
| PBS | + |
| Na acetate | + |
| Na acetate/$Cu^{2+}$ | ++ |
| LB | + |

The bacterial DNA is extracted from the bacteria which have been captured by the microbeads; the bacteria are lysed by adding 100 μl of "Chelex 30%" to the microbeads. The mixture is incubated for 10 minutes at 95° C.; then centrifugation is carried out for 10 minutes at 10,000 rpm. The supernatant containing the DNA is stored at −20° C.

47 μl of the amplification solution (AquaPure Genomic DNA Isolation KIT) is added to 3 μl of the extracted DNA; the final concentrations are as follows:

5 μl: 200 mM dXTP
10 μl: Buffer 5×
5 μl: 2 mM MgCl$_2$
1 μl of each primer: (primer diluted to 200 mL):

```
27:GTGCTGCAGAGAGTTTGATCCTGGCTCAG (sense;
SEQ ID NO: 1)

1492:CACGGATCCTACGGGTACCTTGTTACGACTT (antisense;
SEQ ID NO: 2)
```

1 μl: Taq polymerase, 5 u/μL
WFI water qsf 50 μL

After homogenization, the reaction mixtures are placed in an "Eppendorf" thermocycler and subjected to the following programme:

$$\left.\begin{array}{l} 94°\ C.: 1\ mn \\ 60°\ C.: 1\ mn \\ 72°\ C.: 1\ mn \\ 72°\ C.: 1\ mn \end{array}\right\} 35\ cycles$$

The DNAs are then maintained at 10° C. The migration takes place on a 2% agarose gel in PBE buffer 0.5× containing ethidium bromide. The gel is then observed under UV light. The results of the PCR clearly indicate the presence of a bacterium: a strong positive signal is noted. The identification of the bacterium is then carried out by sequencing in known manner. The PCR shows the presence of bacterial DNA on the microbeads irrespective of the buffer used with a stronger signal in the case of the acetate buffer in the presence of $Cu^{2+}$ Secondly, analogous tests were also carried out with the bacteria *Pseudomonas aeruginosa*, *Streptococcus pneumoniae* and *Staphylococcus aureus* and have produced the same type of results.

EXAMPLE 2

Binding of the Herpes Virus OsHV-I in Copper Medium on Microbeads Loaded with β2GPI This virus exists in oysters. A homogenate of oysters is produced, from which the DNA is extracted by PCR using magnetic microbeads loaded with β2GPI. These loaded microbeads are prepared as indicated in Example 1.

100 mg of young oysters are ground in 500 μl of water of milli-Q quality. The homogenate (50 μl) is diluted in two different buffers, namely a PBS buffer (pH=7-7.4) (composition identical to that of Example 1) and an acetate/$Cu^{2+}$ buffer (pH=5.6) having the composition defined in Example 1.

Quantities of microbeads loaded with 10, 20 or 50 μL are added to 500 μL of what thus constitutes two fluid media M. The beads are then incubated at 37° C. for 30 mn and washed twice with PBS buffer. The DNA is finally extracted by adding 100 μl of "Chelex 30%" followed by incubation for 10 mn at 95° C. All the tubes are subjected to centrifugation at 10,000 rpm for 10 nm and the supernatant which contains the DNA is stored.

A PCR is then carried out on 1 μL of the extracted DNA. 19 μL of an amplification solution (Eppendorf HotMaster Taq PCR kit) is added at the following final concentrations:

| Buffer | IX |
|---|---|
| dNTP | 250 μM |
| Primers C2 and C6 | 0.2 μM each |
| Taq Polymerase | 1.5 U |

The primers C2 and C6 are as follows:

```
                                        (SEQ ID NO: 3)
C2 (sense)    = CTCTTTACCATGAAGATACCCACC (SEQ ID NO: 4)
C6 (antisense) = GTGCACGGCTTACCATTTTT
```

The reaction mixture is homogenized and placed in an "Eppendorf Mastercycler" personal thermocycler and subjected to the following programme:

$$\left.\begin{array}{l} -94°\ C.\ 2\ mn \\ -94°\ C.\ 1\ mn \\ -50°\ C.\ 1\ mn \\ -70°\ C.\ 30\ s \\ -70°\ C.\ 5\ mn \end{array}\right\} 35\ cycles$$

The DNA is then stored at 10° C. The same operation is also carried out replacing the homogenate of oysters with 5, 10 then 20 mL of seawater (originating from the oyster bed), the quantity of microbeads loaded with β2GPI then being constant and equal to 50 μL.

By way of comparison, the homogenate of oysters was subjected to a direct extraction of virus DNAs by the two lysis products defined above, without the previous addition of loaded microbeads and the same PCR conditions were used.

In all cases, the DNAs obtained using PCR were used for a Southern Blot on 2% agarose gel in PBE buffer (0.5×) containing ethidium bromide. The gel is then observed under UV light. The set of results is presented in FIG. 1 in which the tracks 1 to 13 represent the experiments defined by Table II:

TABLE II

| Track of FIG. 1 | Experiment |
|---|---|
| 1 | Homogenate + PBS + 10 μl microbeads |
| 2 | Homogenate + PBS + 20 μl microbeads |
| 3 | Homogenate + PBS + 50 μl microbeads |
| 4 | Homogenate + Na acetate/$Cu^{2+}$ + 10 μl microbeads |
| 5 | Homogenate + Na acetate/$Cu^{2+}$ + 20 μl microbeads |
| 6 | Homogenate + Na acetate/$Cu^{2+}$ + 50 μl microbeads |
| 7 | Homogenate + direct Chelex extraction |
| 8 | Homogenate + direct phenol/chloroform extraction |
| 9 | Seawater 5 mL/50 μL microbeads |
| 10 | Seawater 10 mL/50 μL microbeads |
| 11 | Seawater 20 mL/50 μL microbeads |
| 12 | T$^+$ |
| 13 | Tmix |

FIG. 1 shows the same positive signal on tracks 1 to 8: the virus DNA obtained by direct extraction (tracks 7 and 8) is therefore clearly that obtained using microbeads (tracks 1 to 6). All these DNAs were sequenced: the amplicon obtained by the microbeads corresponds to a sequence of 709 bases of the gene of the glycoprotein 1005 of the OsHV-I virus. When the homogenate is diluted in PBS (tracks 1 to 3), the signal is the same irrespective of the quantity of microbeads used whereas in the presence of the $Cu^{2+}$ ions (tracks 4 to 6), the greater the quantity of beads the stronger the signal; moreover, in the presence of $Cu^{2+}$ (tracks 4 to 6), the signal is always stronger than in absence of $Cu^{2+}$ (tracks 1 to 3). This demonstrates the benefit of the presence of the $Cu^{2+}$ ions which improve the detection sensitivity.

On tracks 9 to 11, a signal is seen to appear weakly in the case of track 11, whereas a direct extraction from the seawater had produced a negative result, which also shows that, without the $Cu^{2+}$ ions, the detection by the microbeads is weak.

Track T⁺ is a positive control obtained with the viral DNA sequence in order to establish that the PCR has been successful; the track Tmix is a control obtained with all the ingredients utilized in the PCR but in the absence of the viral DNA.

EXAMPLE 3

Detection of the Hepatitis C Virus (HCV)

50 µL of serum originating from patients infected with the hepatitis C virus is diluted in 500 µL of 50 mM sodium acetate buffer (pH=5.6 with 10 mM of HCl). 10 µL of microbeads loaded with β2GPI, identical to those which have been prepared in Example 1, are added to this medium. Iron, copper, zinc and manganese salts are also added so as to obtain a medium in which the metal ions are present at 2 mM. This mixture is left to incubate at 37° C. for 30 nm, under rotary stirring. A permanent magnet is then moved along the tube which contains the sample, which makes it possible to separate the microbeads from their suspension medium, and the supernatant is removed. The microbeads are subjected to lysis according to the protocol of the "QIAamp Viral RNA mini kit" (Qiagen). Viral nucleic acids are subjected to an RT-PCR protocol: The RT-PCR protocol has been previously described by Young et al. (J. Clin. Microbiol., 1993, 31(4), p. 882-6). 21 µL of the amplification solution (Qiagen One step RT-PCR kit) is added to 4 µL of extracted RNAs in the following final concentrations:

| | |
|---|---|
| Qiagen buffer | 1X |
| dNTP | 400 µM |
| Primers | 0.6 µM each |
| Taq Polymerase | 1.5 U |
| RNase inhibitor | 15 U |

The primers used are as follows

```
                                         (SEQ ID NO: 5)
KY78 (sense):     CAAGCACCCTATCAGGCAGT (SEQ ID NO: 6)
KY80 (antisense): AGCGTCTAGCCATGGCGT
```

After homogenization the reaction mixtures are placed in a thermocycler (Eppendorf personal Mastercycler) and subjected to the following programme:

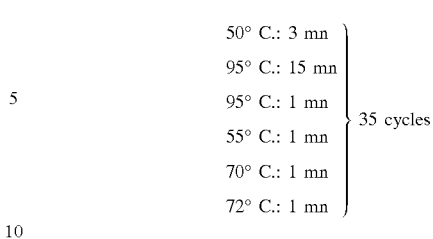

Figure 2:
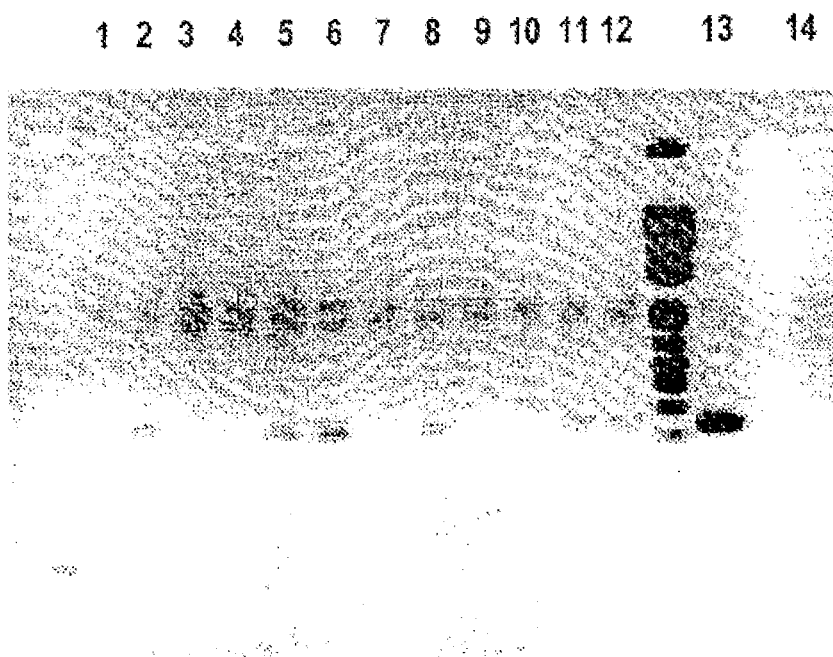

The DNAs are then maintained at 4° C. and a Southern Blot is carried out corresponding to FIG. 2.

FIG. 2 shows that in the presence of $Cu^{2+}$, the sensitivity of detection of the hepatitis C virus is clearly improved. By contrast, in the presence of $Zn^{2+}$, the virus is not detectable, irrespective of the pH of the sample.

Figure 3:
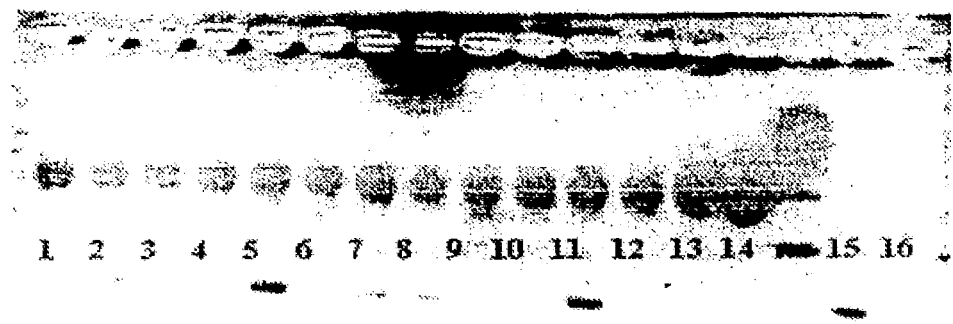

FIG. 3 shows the results obtained for a sample (serum or plasma) containing 130 copies of viral genome per mL of sample. The definition of the samples corresponding to the 16 tracks is given in Table III. In FIG. 3 it is noted that in the absence of magnetic microbeads loaded with β2GPI, there is no signal showing the viral presence: the sensitivity limit of the method used has been reached. On the other hand, in the presence of $Cu^{2+}$, the signal of the virus becomes visible.

TABLE III

| Track No. | Sample tested |
|---|---|
| 1 | serum pH 7.6 + 6 microbeads |
| 2 | serum pH 7.6 + $Cu^{++}$ + microbeads |
| 3 | serum pH 7.6 + $Fe^{++}$ + microbeads |
| 4 | serum pH 5.6 + microbeads |
| 5 | serum pH 5.6 + $Cu^{++}$ + microbeads |
| 6 | serum pH 5.6 $Fe^{++}$ + microbeads |
| 7 | plasma pH 7.6 + microbeads |
| 8 | plasma pH 7.6 + $Cu^{++}$ + microbeads |
| 9 | plasma pH 7.6 + $Fe^{++}$ + microbeads |
| 10 | plasma pH 5.6 + microbeads |
| 11 | plasma pH 5.6 + $Cu^{++}$ + microbeads |
| 12 | plasma pH 5.6 + $Fe^{++}$ + microbeads |
| 13 | serum detection in the absence of microbeads |
| 14 | plasma detection in the absence of microbeads |
| 15 | positive control |
| 16 | negative control |

Figure 4:
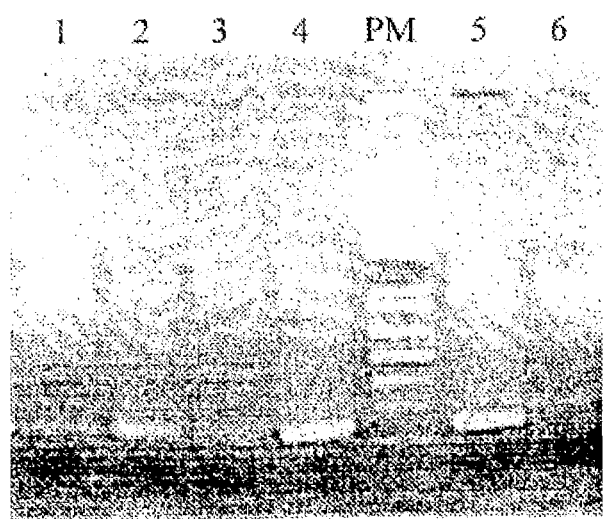

It has moreover been established that the $Cu^{2+}$ ions act on the sample and not on the microbeads. In order to do this, 2 mM copper acetate is added to the microbeads loaded with β2GPI followed by incubation at 37° C. for 30 nm under stirring. The microbeads have then been rinsed and brought into contact with the sample of serum containing no $Cu^{2+}$. Table IV identifies the nature of the test corresponding to each of tracks 1 to 6 in FIG. 4.

TABLE IV

| Track No. | Nature of the test |
|---|---|
| 1 | β2GPI + $Cu^{++}$ + washing + HCV |
| 2 | β2GPI + $Cu^{++}$ + HCV |
| 3 | HCV in the absence of β2GPI |
| 4, 5 | Positive control |
| 6 | Negative control |
| PM | Molecular weight |

EXAMPLES 4 to 8

Detection of Other Viruses

Test protocols identical to those which have been described above in Examples 2 or 3 were used depending on whether DNA or RNA viruses respectively were involved.

It was noted that for all these viruses, the results were the same as those described in Examples 2 or 3. The viruses which were the subject of these tests are: the West Nile viruses, Andes Hantavirus type virus, Dengue virus sub-types 1, 2, 3 and 4, HIV 1 and 2 virus, and H1N1 and H1N2 influenza virus.

EXAMPLE 9

Capture of the H3N2 Influenza Virus by Microbeads in Copper Medium and Use of the Microbeads Loaded with Viruses for the Visual Detection of Said Viruses A pharyngeal sample from a patient suffering from influenza is diluted in MEM culture medium (Eagle's minimum essential medium) containing 2 mM of copper sulphate. 10 µL of microbeads as prepared in Example 1 are added: these microbeads are therefore loaded with ß2GP1. The microbeads are brought into contact with 500 µL of the medium in which the sample is situated, the whole mixture being placed in a 2 mL Eppendorf tube. The mixture is incubated at 37° C. under rotary stirring for 30 nm. The tube is then placed in contact with a permanent magnet; the microbeads are attracted by the magnetic field against the wall; the supernatant is aspirated and removed. 1.5 mL of PBS buffer (composition given in Example 1) is introduced into the tube in order to obtain a suspension of microbeads; the tube is replaced in contact with the permanent magnet and the supernatant is aspirated and removed. This operation of washing the microbeads is repeated three times in total, then the microbeads are resuspended in 1 mL of MEM culture buffer.

The suspension thus obtained is brought into contact with MDCK cells at 37° C. for 24 hours. The cells are then washed twice in physiological serum and fresh MEM culture medium is added and the cells are cultured for 4 days at 37° C. The infection is verified either by the cytopathogenic effect of the virus after staining the cells with crystal violet (see FIG. 5), or by immunofluorescence, after binding of the cells with acetone and reaction with fluorescent monoclonal antibodies, which recognize the viral proteins (FIGS. 6A and 6B).

Figure 5:
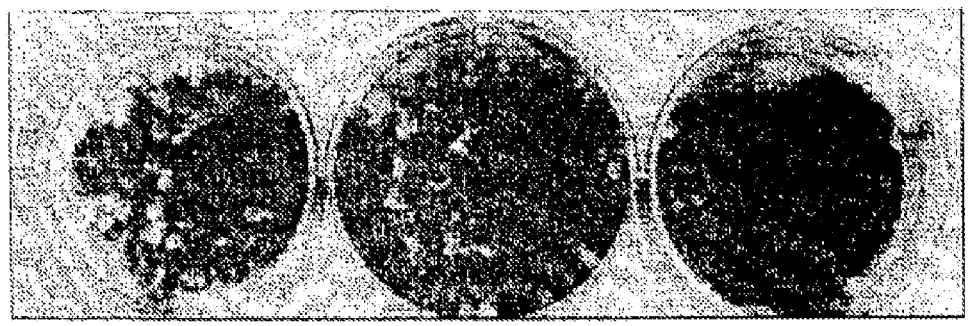

In FIG. 5, the Petri dish on the left corresponds to 6000 pfu of virus (1 pfu makes it possible to form a lysis site), the view in the centre corresponds to 2000 pfu of viruses and the view on the right corresponds to 200 pfu of viruses. The progressive disappearance of the cells shows that the microbeads certainly carried viruses with cytopathogenic effect.

Figure 6A:
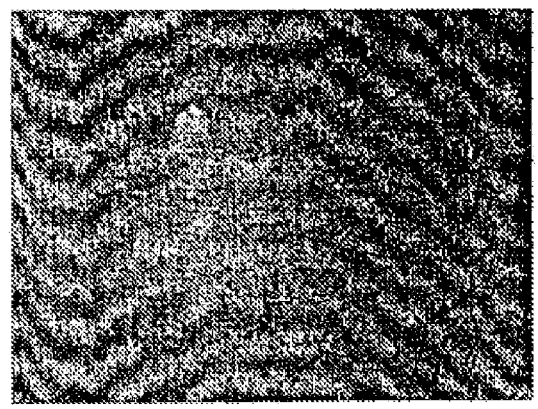
Figure 6B:
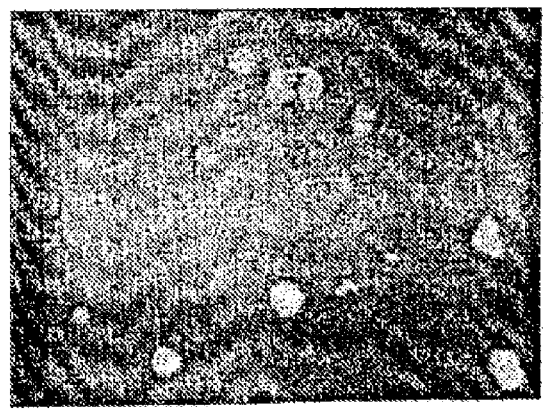

In FIG. 6A, it can be seen that the cells carrying the viral proteins are located by fluorescence: the culture medium containing the viral sample is brought directly into contact with the MDCK cells and it is noted that few cells are fluorescent which shows that the capture of the virus was insignificant when the microbeads are not used. FIG. 6B shows the result obtained with the use of the microbeads: it is thus established that the microbeads have concentrated the sample viruses, which therefore allows a detection with a much smaller viral load.

EXAMPLE 10

Capture of the Virus of the Vaccine by Microbeads Loaded with ß2GPI and Use of the Latter to Infect Cells The same protocol as that described in detail in Example 9 is applied for the infection of the Hep 2 cells, with the virus of the vaccine captured by the microbeads loaded with ß2GP1. For this example, a virus suspension making it possible to form 1000 lysis sites (1000 pfu) was used.

Figure 7A:
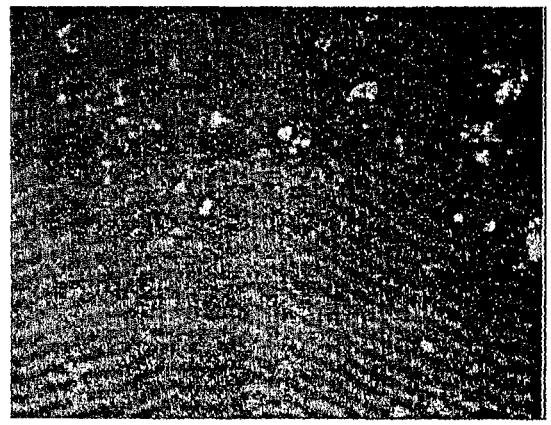
Figure 7B:
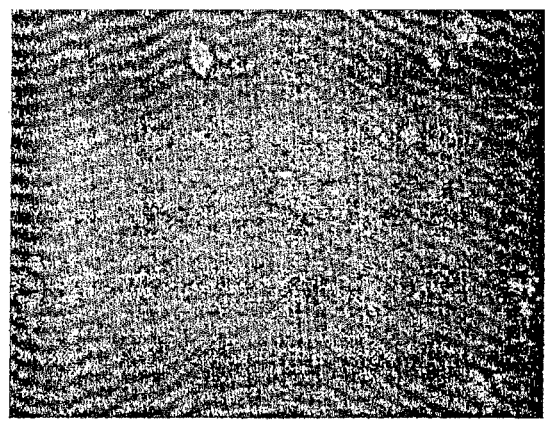

FIG. 7A shows the situation when the virus of the vaccine has been captured by microbeads loaded with ß2GP1: it can be seen that numerous cells have been infected. By contrast, FIG. 7B shows the case where the Hep 2 cells have been infected with the virus of the vaccine in the absence of microbeads loaded with ß2GP1: it can be seen that the number of fluorescent cells is much more restricted, which makes it possible to conclude that the microbeads loaded with ß2GPI have made it possible to concentrate the viruses used, since the quantity of virus was the same for the tests in FIGS. 7A and 7B.

Figure 7C:
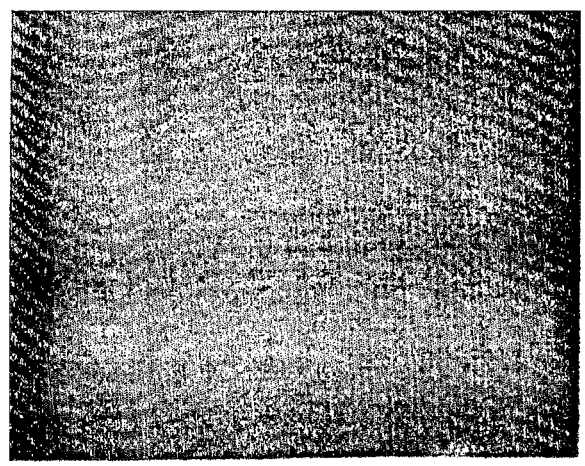

FIG. 7C shows Hep 2 cells brought into contact with the washing buffer of the microbeads after they have been loaded with ß2GPI and viruses of the vaccine: it is noted that there is an absence of fluorescence, which means that the washing buffer has not carried away any of the viruses bound to the microbeads.

It is therefore noted that the microbeads loaded with ß2GPI make it possible to improve the sensitivity of detection of the viruses.

The invention claimed is:

1. An in vitro method for detection and/or quantification and/or identification of viruses present in a fluid medium M constituting a biological material, in which, in a known manner, a suspension of microbeads in a liquid suspension medium is prepared, said microbeads being delimited by an outer surface constituted by a solid polymer material capable of binding proteins, the method comprising the following stages:

a) a loading of the microbeads in the suspension with β2GPI proteins is ensured by coupling with a sufficient quantity of β2GPI proteins, either passively in a suspension medium or using a known chemical binding protocol;

b) in a container, said microbeads loaded with β2GPI proteins are brought into contact with the fluid medium M by adding ions of at least one oxidizing metal, under appropriate conditions in order to ensure sufficient binding of the viruses to the β2GPI proteins carried by the microbeads;

c) the microbeads thus prepared are separated from their suspension medium, said suspension medium is removed from the container in order to obtain, optionally after washing with a buffer, a residue with a high concentration of viruses;

d) and the viruses are detected and/or quantified and/or identified, starting from the concentrated residue thus obtained.

2. The method according to claim 1, wherein the loading of the microbeads in stage a) is carried out passively in a buffer having a pH comprised between 3.5 and 10.5, by incubating, for a period of time comprised between 10 minutes and 24 hours, at a temperature comprised between 4 and 40° C.

3. The method according to claim 1, wherein the loading of the microbeads with β2GPI proteins is carried out by placing them in a liquid suspension medium which contains, in aqueous solution, from $10^{-6}$ to 100 mg of β2GPI per gram of dry weight of microbeads, the concentration of β2GPI in the medium being comprised between $10^{-5}$ and 10 μg/μl.

4. The method according to claim 1, wherein the loading of the microbeads with β2GP1 proteins is carried out in a buffer having a pH comprised between 5 and 9 with incubation for a period of time comprised between 10 minutes and 24 hours at a temperature comprised between 4 and 40° C.

5. The method according to claim 1, wherein, in stage b), the ions of oxidizing metal added to the medium M are copper ions, the concentration of copper ions in the medium M being comprised, after said addition, between 1 mM and 100 mM.

6. The method according to claim 1, wherein the solid material constituting the outer surface of the microbeads is chosen from the group formed by the plastics and the elastomers, said material carrying or not carrying reactive groups grafted to the outer surface of the microbeads in order to ensure a chemical bond to the β2GPI proteins.

7. The method according to claim 1, wherein microbeads having a substantially spherical shape and an average diameter comprised between 1 and 100,000 nm are chosen.

8. The method according to claim 1, wherein microbeads having a core formed by one (or more) particle(s) of magnetic material are chosen in order to allow their separation from the suspension medium using a magnetic field.

9. The method according to claim 1, wherein the microbeads are separated from their suspension medium by centrifugation.

10. The method according to claim 1, wherein stage d) is carried out by a means taken from the group formed by infectivity, a specific enzymatic reaction, a fluorescent or radiolabelled tracer, a detection of specific nucleic acids by hybridization with a labelled probe, a PCR or RT-PCR reaction, an assay, a count, a visualization, an optical method, electron or non-electron microscopy.

11. The method according to claim 1, wherein, starting from the concentrated residue, the nucleic acids of the viruses of interest are extracted by lysis, followed by PCR or RT-PCR amplification of said nucleic acids by using the primers appropriate to said viruses of interest and visualization on gel of the nucleic acids optionally obtained in order to define the presence or the absence of the viruses of interest and/or in order to quantify the viral load of said viruses of interest in the medium M.

12. The method according to claim 1, wherein, in order to detect and/or identify viruses of interest bound to microbeads obtained according to stage c), the residue is resuspended, the microbeads are brought into contact with cells sensitive to the viruses of interest, said cells are cultured and any infection of the cells by the viruses of interest is observed.

13. The method according to claim 12, wherein, in order to detect an infection of cells, the cytopathological effect of the viruses after appropriate staining of the cells, or the immunofluorescence after binding of the cells and reaction with fluorescent antibodies which recognize proteins corresponding to the presence of the viruses, are observed.

* * * * *